(12) United States Patent  
Sayani et al.

(10) Patent No.: US 11,007,344 B2
(45) Date of Patent: May 18, 2021

(54) RESUSCITATION DEVICE

(71) Applicant: The Aga Khan University, Karachi (PK)

(72) Inventors: Saleem Sayani, Wynnewood, PA (US); Muhammad Abdul Muqeet, Karachi (PK); Hafiz Imtiaz Ahmed, Karachi (PK); Naeem Sheikh, Karachi (PK); Sannan Ahmed Qureshi, North Karachi (PK); Huba Atiq, Karachi (PK); Syeda Zoha Raza, Hyderabad (PK); Khawaja Mohammad Inam Pal, Karachi (PK); Syed Shujaat Hussain, Karachi (PK); Maleeha Naseem, Karachi (PK); Amna Jawaid, Karachi (PK); Jonathan Johnson, Karachi (PK)

(73) Assignee: The Aga Khan University, Karachi (PK)

( * ) Notice: Subject to any disclaimer, the term of this patent is extended or adjusted under 35 U.S.C. 154(b) by 214 days.

(21) Appl. No.: 15/923,666

(22) Filed: Mar. 16, 2018

(65) Prior Publication Data

US 2019/0232016 A1 Aug. 1, 2019

(30) Foreign Application Priority Data

Jan. 31, 2018 (PK) ........................................ 62/2018

(51) Int. Cl.
*A61M 16/20* (2006.01)
*A61M 16/10* (2006.01)
(Continued)

(52) U.S. Cl.
CPC ...... *A61M 16/202* (2014.02); *A61M 16/0084* (2014.02); *A61M 16/04* (2013.01);
(Continued)

(58) Field of Classification Search
CPC .............. A61M 16/00; A61M 16/0057; A61M 16/0072; A61M 16/0075; A61M 16/0084;
(Continued)

(56) References Cited

U.S. PATENT DOCUMENTS 177,082 A  *  5/1876  Strout .................... B65D 43/26
                                                    217/60 B
2,547,458 A  *  4/1951  Goodner ............... A61M 16/00
                                                    128/204.25
(Continued)

FOREIGN PATENT DOCUMENTS

WO    WO-2016203289 A1 * 12/2016 ........ A61M 16/0084

OTHER PUBLICATIONS

MIT Technology Review Pakistan, "Pakistani Engineer Braves Tragedy to Develop Low Cost Ventilator", retrieved from http://www.technologyreview.pk/pakistani-engineer-braves-tragedy-to-develop-low-cost-ventilator; dated Sep. 5, 2016.*

(Continued)

*Primary Examiner* — Joseph D. Boecker
(74) *Attorney, Agent, or Firm* — Fish & Richardson P.C.

(57) ABSTRACT

A resuscitation device is described that can include an electronic circuit board, a shaft that is operably coupled with the electronic circuit board and has a head, a gas-bag adjacent to the head and configured to store gas, and a valve operably coupled to the gas-bag. The electronic circuit board can actuate the shaft to move. The moving of the shaft can cause the head to compress the gas-bag. The compression of the gas-bag can cause the gas-bag to release gas. Related apparatuses, systems, methods, techniques and articles are also described.

20 Claims, 7 Drawing Sheets

(51) Int. Cl.
*A61M 16/00* (2006.01)
*A61M 16/06* (2006.01)
*A61M 16/04* (2006.01)

(52) U.S. Cl.
CPC .......... *A61M 16/06* (2013.01); *A61M 16/107* (2014.02); *A61M 2202/0208* (2013.01); *A61M 2205/3331* (2013.01); *A61M 2205/502* (2013.01); *A61M 2205/8206* (2013.01); *A61M 2240/00* (2013.01)

(58) Field of Classification Search
CPC .. A61M 16/022; A61M 16/024; A61M 16/04; A61M 16/06; A61M 16/107; A61M 16/202; A61M 16/204; A61M 16/208; A61M 2205/3331; A61M 2205/50; A61M 2205/502; A61H 31/02
See application file for complete search history.

(56) References Cited

U.S. PATENT DOCUMENTS

| | | | | |
|---|---|---|---|---|
| 3,757,776 | A * | 9/1973 | Bauman | A61M 16/0057 128/202.22 |
| 5,222,491 | A * | 6/1993 | Thomas | A61M 16/0084 128/205.13 |
| 2005/0284472 | A1* | 12/2005 | Lin | A61M 16/0057 128/202.29 |
| 2008/0257351 | A1 | 10/2008 | Gitschlag | |
| 2011/0041852 | A1* | 2/2011 | Bergman | A61M 16/0078 128/205.13 |
| 2012/0145151 | A1* | 6/2012 | Bergman | A61M 16/0078 128/204.21 |
| 2014/0150791 | A1* | 6/2014 | Birnkrant | A61M 16/024 128/204.23 |
| 2014/0275820 | A1* | 9/2014 | Varga | A61M 16/0078 600/301 |
| 2014/0318544 | A1* | 10/2014 | Murphy | A61M 16/0075 128/205.14 |
| 2017/0197047 | A1* | 7/2017 | Minato | A61M 16/0078 |
| 2018/0296788 | A1* | 10/2018 | Merrell | A61M 16/0883 |
| 2020/0353192 | A1* | 11/2020 | Fried | A61M 16/0084 |

OTHER PUBLICATIONS

MIT News, "In the World: Breath of life", retrieved from news.mit.edu/2010/itw-ventilator-0715; dated Jul. 15, 2010.*

"Medical Technology Innovation by Dayo Olakulehin", retrieved from https://www.youtube.com/watch?v=sl2d7PTQUmw; dated Jan. 11, 2018.*

"Innovation app wins top prize at AKU's first-ever Hackathon." Aug. 16, 2016. 3 pages. Web. Mar. 20, 2018.; https://www.aku.edu/news/Pages/News_Details.aspx?nid=NEWS-000212.

Padmasini, N. and J. Archana. "An Automated Breathing Device for Critically Ill Patients." R. Malathi and J. Krishman (eds), *Recent Advancements in System Modelling Application*, Lecture Notes in Electrical Engineering 188. Chapter 35. Springer, India. (2013). pp. 405-411.

* cited by examiner

RESUSCITATION DEVICE

RELATED APPLICATION

This disclosure claims priority to Pakistan Patent Application No. 62/2018, filed on Jan. 31, 2018, and entitled "Resuscitation Device", the entire contents of which are hereby fully incorporated by reference.

TECHNICAL FIELD

The subject matter described herein relates to a resuscitation device that can control and monitor the amount and frequency of gas (e.g., oxygen) being supplied to a patient.

BACKGROUND

Resuscitation devices are known to provide emergency oxygen to patients. Traditionally, such devices are bulky, and usually present in hospitals, clinics, and ambulances. The conventional resuscitation devices are usually complex to use, and for at least this reason clinicians are required to operate them. For example, a clinician may be required to hold the mask over a mouth and/or nose of the patient, and another clinician may be required to operate the resuscitation device. The resuscitation device may have a bag, which when squeezed may provide oxygen. The other clinician that operates the resuscitation device may operate the device by squeezing the bag at a predetermined frequency. However, when the other clinician does not squeeze the bag enough, the oxygen provided to the patient may not be sufficient. If the other clinician keeps squeezing the bag, the oxygen provided to the patient may become excessive, and may go to the stomach, causing gastric insufflation, rather than to the lungs of the patient. There, accordingly, exists a need to have a resuscitation device that is easily portable, light in weight, and easy to use, and can control and monitor the pressure and frequency of oxygen being supplied to a patient.

SUMMARY

In one aspect, a resuscitation device is described that can include an electronic circuit board, a shaft that is operably coupled with the electronic circuit board and has a head, a gas-bag adjacent to the head and configured to store gas, and a valve operably coupled to the gas-bag. The electronic circuit board can actuate the shaft to move. The moving of the shaft can cause the head to compress the gas-bag. The compression of the gas-bag can cause the gas-bag to release gas.

In some variations, one or more of the following can be implemented either individually or in any feasible combination. The resuscitation device can further include a programmable computer configured to receive an input. The programmable computer can be operably coupled to the electronic circuit board. The electronic circuit board can actuate the shaft to move upon the receipt of the input. The programmable computer can receive the input from a user. The programmable computer can receive the input from a computer of a clinician via a communication network. At least one of the programmable computer and the electronic circuit board can implement a self-adjusting algorithm to control a pressure of the released gas and a frequency at which the gas is released. The programmable computer and the electronic circuit board can be operably coupled via a wired connection. The programmable computer can be configured to display, on a graphical user interface, a pressure of the released gas and a frequency at which the gas is released. The programmable computer can be configured to receive another input to control the movement of the shaft so as to control a pressure of the released gas and a frequency at which the gas is released.

The resuscitation device can further include a mask operably coupled to the gas cylinder. The mask can interface with at least one of a mouth and a nose of a user. The resuscitation device can additionally or alternately include (that is, include, as an addition or alternate to the mask) an endotracheal tube operably coupled to the gas cylinder. The endotracheal tube can be intubated into the user. The resuscitation device can further include a gas cylinder attached to the gas-bag. The gas cylinder can fill the gas-bag with gas after the gas-bag has released gas. The resuscitation device can further include one or more clips configured to attach with a railing of at least one of a bed and a stretcher. The valve can include a filter configured to purify the gas being released by the gas-bag.

In another aspect, a programmable computer of a device can receive an input to control movement of a shaft within the device. The shaft can have a head. Based on the input, a controller on an electronic circuit board wired to the programmable computer can move the shaft with the head. The movement of the head can cause the head to press against a gas-bag within the device to compress the gas-bag. The gas-bag can release gas when the gas-bag has been compressed. The gas can be released by the gas-bag via a valve operably coupled to the gas-bag. A gas cylinder attached to the gas-bag can fill the gas-bag with additional gas after the release of gas.

In some variations, one or more of the following can be implemented either individually or in any feasible combination. The input can include a height of a patient, a weight of a patient, and a type of a patient. The type of the patient can be one of neonatal, pediatric, and adult. At least one of the programmable computer and the electronic circuit board can implement a self-adjusting algorithm to control, based on the input, a pressure of the released gas and a frequency at which the gas is released so that the released gas has a preset pressure and is released at a preset frequency. A graphical user interface of the programmable computer can display a pressure of the released gas and a frequency at which the gas is released. The gas-bag can be locked in place using one or more detachable rods of the device.

The subject matter described herein provides many advantages, including the following. The resuscitation device can be: light-in-weight, easily portable, used anywhere at the convenience of a user and solely by the user, and easy and simple to use. The resuscitation device can provide gas to a user without requiring a manual squeezing of the gas-bag. The gas provided can be controlled and monitored by the user, thereby preventing inadequate or excessive gasification (e.g., oxygenation) of the user.

The details of one or more variations of the subject matter described herein are set forth in the accompanying drawings and the description below. Other features and advantages of the subject matter described herein will be apparent from the description, the drawings, and the claims.

BRIEF DESCRIPTION OF DRAWINGS

Like reference symbols in the various drawings indicate like elements.

DETAILED DESCRIPTION

Figure 1:
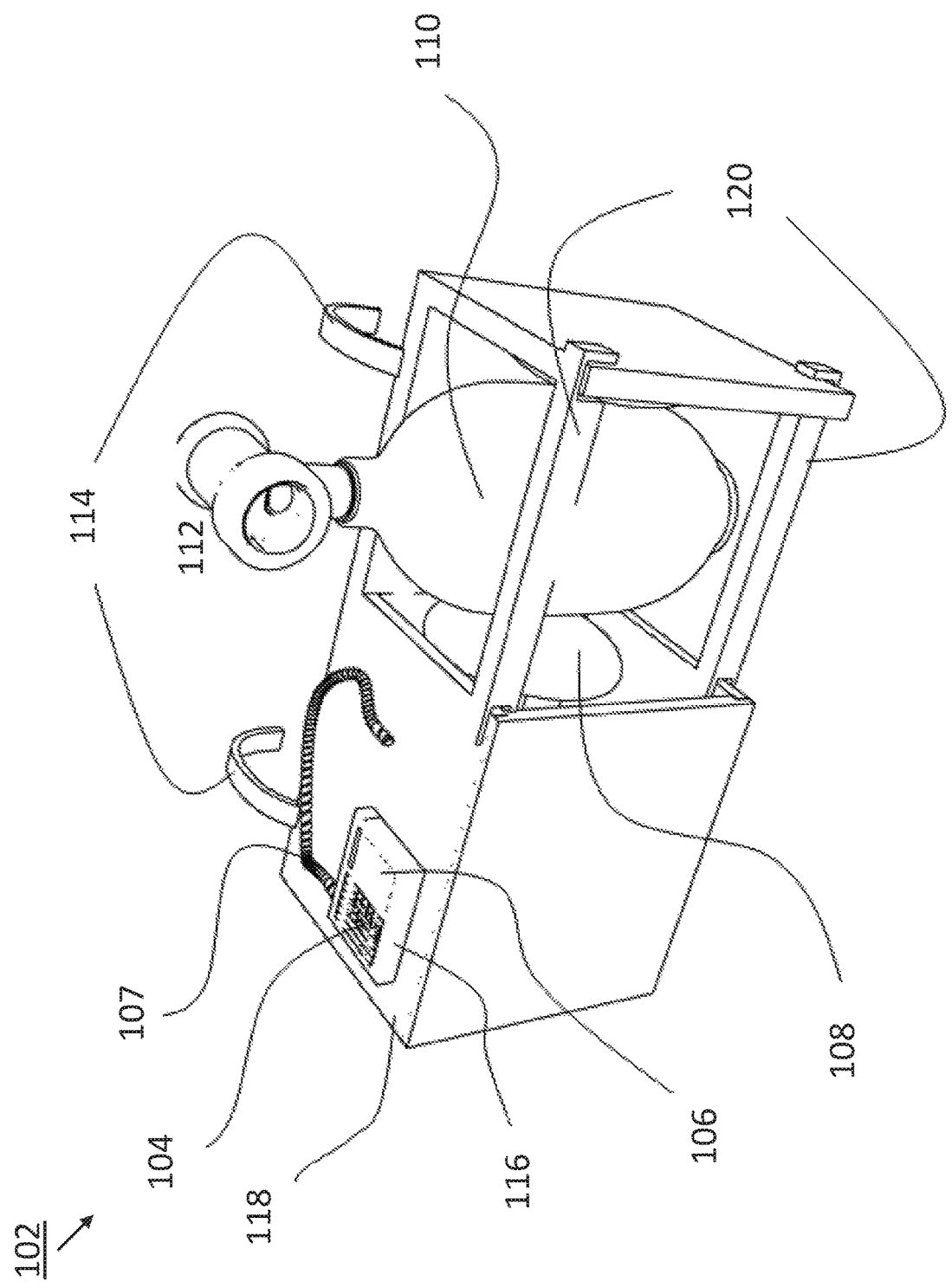
FIG. 1 illustrates one view of a resuscitation device that can control and monitor the amount and frequency of gas being supplied to a user (e.g., patient), in accordance with some implementations of the current subject matter.
Figure 2:
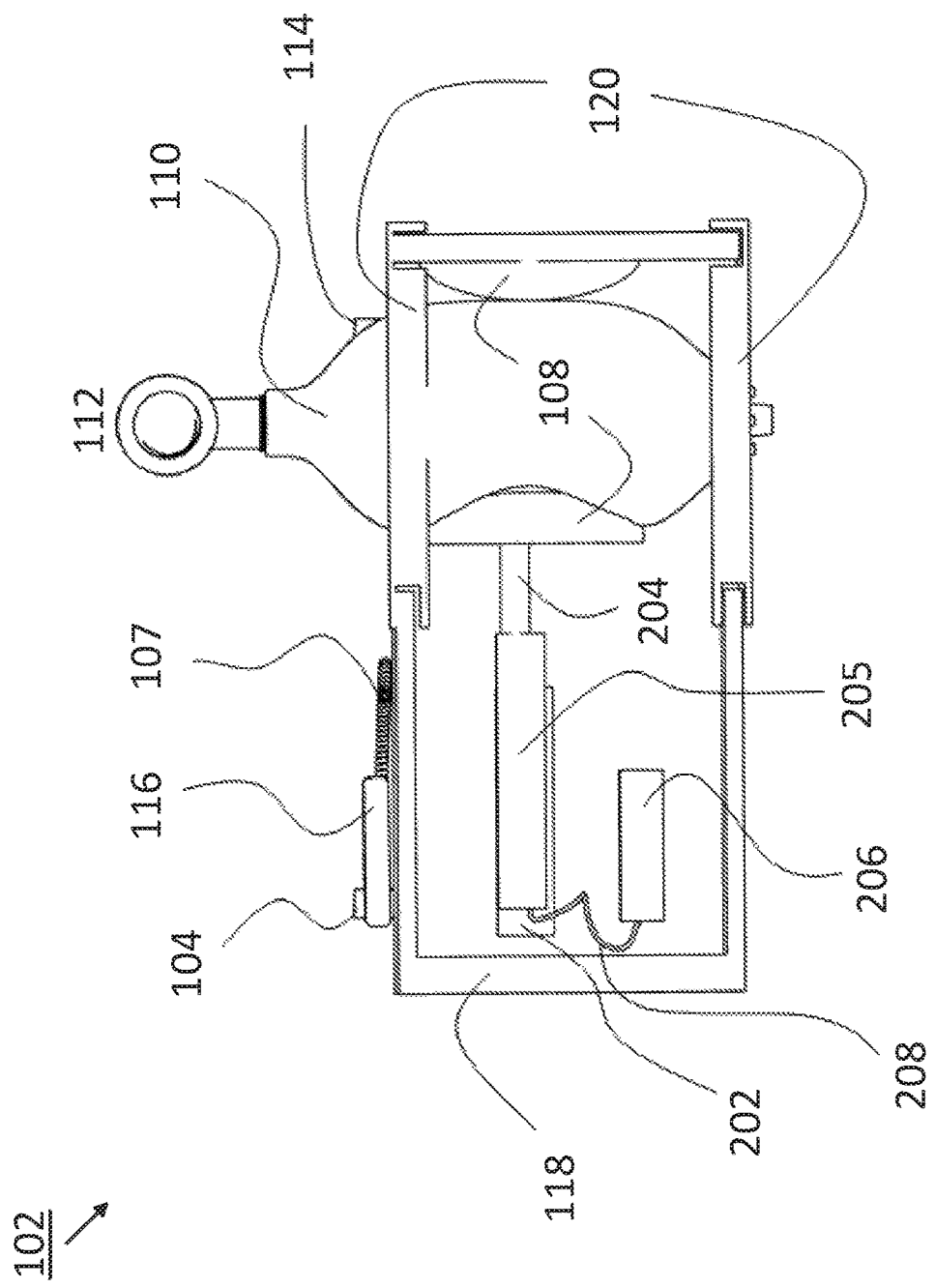
FIG. 2 illustrates an inner cross-sectional view of the resuscitation device, in accordance with some implementations of the current subject matter.

FIG. 1 illustrates one view of a resuscitation device 102 that can control and monitor the amount and frequency of gas (e.g., oxygen) being supplied to a user (e.g., patient). The resuscitation device 102 can include a programmable computer 104 with a display screen 106, an electronic circuit board 202 (shown in FIG. 2) operably coupled to the programmable computer 102 via a wire 107, a shaft 204 (shown in FIG. 2) having a head 108 and being operably coupled to the electronic circuit board 202 (shown in FIG. 2) via an electro-mechanical structure 205 (shown in FIG. 2), a gas-bag (e.g., oxygen bag) 110 adjacent to the head 108, a gas cylinder (not shown; e.g., oxygen cylinder) attached to the gas-bag 110, a valve 112 attached to the gas-bag 110, and a hanging clip 114 attached to the resuscitation device 102. While two heads 108 are shown in FIG. 2, it may be noted that the shaft 204 has a single head 108, which is on the left. The programmable computer 104 can be enclosed in a first housing 116. The resuscitation device 102 can be enclosed in a second housing 118. The resuscitation device 102 can further include a locking system 120 to lock the gas-bag 110 in a single location (i.e., hold the gas-bag 110 in place), and a rechargeable battery 206 (shown in FIG. 2) connected to the electronic circuit board 202 (shown in FIG. 2) via another wire 208 (shown in FIG. 2).

The electro-mechanical structure 205 (shown in FIG. 2) can linearly move based on electrical signals received from the electronic circuit board 202 (shown in FIG. 2), which may be controlled by the programmable computer 104. The linear movement of the electro-mechanical structure 210 (shown in FIG. 2) can linearly move the shaft 204 (shown in FIG. 2) connected to it. The movement of the shaft 204 (shown in FIG. 2) can cause the moved head 108 to compress the gas-bag 110. The compression of the gas-bag 110 can cause the gas stored in the gas-bag 110 to be released via the valve 112. In some implementations, the valve 112 can either include or be attached to a filter to purify the gas released by the gas-bag 110 by filtering-out (i.e., removing) undesirable particles from the gas exiting from the gas-bag 110. The filter can be located immediately before the point-of-use of the gas (e.g., within 2 inches from the proximal of the end valve 112—i.e., the valve 112's end that is closer to the user).

The gas cylinder (not shown), which is attached to the gas-bag 110, can fill the gas-bag 110 with additional gas after the gas-bag 110 has released gas. In one implementation, this filling of additional gas can occur in real-time. In another implementation, the filling of additional gas can occur at predetermined intervals of time.

In FIG. 1, the gas-bag 110 is not being pressed by the head 108, and thus is not compressed, and therefore the gas stored in the gas-bag 110 is not being released. However, in FIGS. 2 and 3, the gas-bag 110 is being pressed by the head 108, and thus is being compressed so as to cause the gas stored in the gas-bag 110 to be released via the valve 112.

The programmable computer 104 can be configured to receive an input from a user. The input can include a height of the patient, a weight of the patient, and a type of the patient. The type of the patient can be one of: neonatal, pediatric, adult, or the like. The patient can interface with the mask of the resuscitation device 102, but may or may not be the user of programmable computer 104. The electronic circuit board 202 (shown in FIG. 2) can initiate the movement of the electro-mechanical structure 205 and therefore the shaft upon the receipt of the input from the user. At least one of the programmable computer 104 and the electronic circuit board 202 (shown in FIG. 2) can implement a self-adjusting algorithm to control, based on the input, the movement of the electro-mechanical structure 205 and the shaft, and thus automatically control a pressure and frequency of the gas released by the gas-bag 110.

The programmable computer 104 can display, on a graphical user interface of the display screen 106, a pressure of the released gas and a frequency at which the gas is released. The programmable computer 104 can be configured to receive, from a user, another input to control the movement of the shaft 204 (shown in FIG. 2) so as to control a pressure of the released gas and a frequency at which the gas is released. The user may provide this other input to adjust the pressure and/or frequency of released gas, which has been displayed to the user on the display screen 106.

The resuscitation device 102 can further include a mask (not shown), which can be operably coupled to the valve 112. The mask can be configured to interface with a mouth and/or a nose of a user. The mask can have different sizes so that masks are available of people of different sizes, such as infants, children, and adults. Additionally or alternately, the resuscitation device 102 can further include an endotracheal tube operably coupled to the valve 112. The endotracheal tube can be configured to be intubated into the user. The endotracheal tube can have different sizes to fit different people, such as infants, children, and adults. While the mask and the endotracheal tube are described as being a part of the resuscitation device 102, in alternate implementations, the mask or the endotracheal tube may be operably coupled to the valve 112 but may not be a component of the resuscitation device 102.

The hanging clip 114 can be configured to attach the resuscitation device 102 with a structure, such as a railing of a bed, a stretcher, or other structure. While a clip 114 is described, in alternate implementations any other attachment structure can instead be used, such as one or more of: a clasp, a hasp, a catch, a hook, a buckle, a lock, any other attachment structure, and any combination thereof.

While the programmable computer 104 and the electronic circuit board 202 (shown in FIG. 2) are described as being connected via the wire 107, in alternate implementations the programmable computer 104 and the electronic circuit board 202 can be communicatively coupled via a wireless connection, which can be one or more of: local area network, internet, wide area network, metropolitan area network, BLUETOOTH network, infrared network, wired network, and any other communication network. Further, while the electronic circuit board 202 (shown in FIG. 2) and the rechargeable battery 206 (shown in FIG. 2) are described as being connected via the wire 208 (shown in FIG. 2), in alternate implementations the electronic circuit board 202 and the rechargeable battery 206 can be communicatively coupled via a wireless connection, which can be one or more of: local area network, internet, wide area network, metropolitan area network, BLUETOOTH network, infrared network, wired network, and any other communication network.

The programmable computer 104 and the display screen 106 are described in greater detail below by FIG. 7. In one implementation, the programmable computer 104 can communicate with a back-end server, which can further communicate with a clinician's computer so that the clinician can remotely diagnose the user and/or control the operation of the resuscitation device 102. For example, the clinician can provide, as input to the programmable computer 104, the ideal specifications of the frequency and pressure at which the gas should be released. The programmable computer 104 can communicate with the back-end server via a communication network, such as one or more of: local area network, internet, wide area network, metropolitan area network, BLUETOOTH network, infrared network, wired network, and any other communication network. The clinician's computer can also communicate with the back-end server via the same or another communication network, which can be one or more of: local area network, internet, wide area network, metropolitan area network, BLUETOOTH network, infrared network, wired network, and any other communication network. The back-end server can be a cloud-computing server.

The use of a cloud-computing server can be advantageous over a traditional server, as the cloud computing server can permit a quick scalability by addition of additional web services within in a few seconds. When the load on software applications running on the programmable computer 104 or the clinician's computer increases, additional processors or databases can be added—or alternately the processing abilities of the existing processors or databases can be enhanced—within a few seconds. Additionally, the cloud-computing server can advantageously enable: a dynamic provisioning, monitoring and managing of the web services on the programmable computer 104 and the clinician's computer, as well as an easy and a quick (e.g., within a few seconds) restoring those services to a previous version if and when required.

The electronic circuit board 202 (shown in FIG. 2) can be an electronic chip/circuit that can include a controller that communicates with the at least one processor of the programmable computer 104. The wire 107 can be a helical wire. The use of helical wire can be advantageous to prevent entangling of the wire 107 while the resuscitation device 102 is being used. While the wire 107 is described as being a helical wire, in alternate implementations the wire 107 can have any other type of structure. In some implementations, the wire 107 can be one or more of: an unshielded twisted pair (UTP) cable, a shielded twisted pair (STP) cable, a coaxial cable, a fiber optic cable, a cable installation guide, and the like. The wire 208 (shown in FIG. 2) can also be any type of electrical wire. In some implementations, the wire 208 can be one or more of: an unshielded twisted pair (UTP) cable, a shielded twisted pair (STP) cable, a coaxial cable, a fiber optic cable, a cable installation guide, and the like.

The electro-mechanical structure 205 (shown in FIG. 2) can also be referred to as an actuator, an electro-mechanical actuator, a linear actuator, or the like. The shaft 204 can be cylindrical, and can have a cross-section of a circular shape. The cylindrical structure and circular shape of cross-section can ensure that the shaft 204 most effectively transfers the force of the electro-mechanical structure 205 to the head 108 to compress the gas-bag 110, thereby ensuring accuracy in measurements of pressure and frequency of the released gas. In alternate implementations, the shaft 204 may have alternate structures and cross-sections. For example, the cross-section of the shaft 204 may instead be oval, rectangular, polygonal, or irregular in shape, in various corresponding implementations. The head 108 may have the shape shown in the drawing, as such shape can be most effective for compressing the gas-bag 110 and accurately measuring the pressure and frequency of the released gas.

The gas-bag 110 can also be referred to as an ambulatory bag, a resuscitation bag, or the like. While oxygen is described above as an example of the gas, in alternate implementations any other gas can be used depending on the purpose for which the resuscitation device 102 is being used. For example, the gas can be one or more of: carbon-dioxide, nitrogen, helium, neon, krypton, xenon, any other gas, and any combination thereof with or without oxygen.

The valve 112 can be a one-way valve that sends/allows gas into the user. The filter within the valve 112 can be one or more all-welded depth filters, one or more high pressure filters, and one or more high purity membrane filters. The first housing 116 of the programmable computer 114 can be made of plastic, metal, alloy, any other material, or any combination thereof. The second housing 118 of the resuscitation device 102 can be made of plastic, metal, alloy, any other material, or any combination thereof.

The gas-bag 110 can be locked using an interlocking mechanism, which involves removable/detachable rods 120. The rods 120 can be inserted to lock the gas-bag 110 firmly in place. The rods 120 can be removed or detached to, for example, change or replace the gas-bag 110.

The rechargeable battery 206 (shown in FIG. 2) can be a lithium ion battery or a lithium ion polymer battery, as these batteries are small and light in weight. These batteries can advantageously keep the weight of the resuscitation device 102 low, have a high-energy density allowing higher capacities, have a low self-discharge, have minimal maintenance needs, have a flexible form factor so that they do not need to be of any particular shape, and provide an improved safety—i.e., are more resistant to overcharge and low chance of electrolyte leakage. While lithium ion and lithium ion polymer batteries are described, in alternate implementations, the rechargeable battery 206 can be a nickel cadmium battery, a nickel-metal hydride battery, a lead acid batter, or any other rechargeable battery. While the battery 206 is described as being rechargeable, in an alternate implementation the battery may not be rechargeable. For example, the battery 206 may instead be an non-rechargeable alkaline batteries (e.g., non-rechargeable AA or AAA batteries).

The resuscitation device 102 can be 9.5 inches in width, 3.7 inches in height, and 6.5 inches in depth. The resuscitation device 102 can have a weight ranging from 400 grams to 1000 grams, based on size of the gas-bag 110 and the number of batteries within the resuscitation device 102. The first housing 116 can have a width and height of 3 inches and depth of 1 inches, with a wire 107 of length 8 inches. The hanging clips 114 can have a 180 degree angle with a diameter of 2.5 inches, a height of 2 inches, and a thickness of 1 inch. The heads 108 can be D-shape blocks, each having a diameter of 3 inches and thickness of 0.5 inches from the center, and 0.2 inch at the edges of the block. The electromechanical structure 205 can have a length of 4 inches with a shaft that can extend up to 2 inches when fully extended.

FIG. 2 illustrates an inner cross-sectional view of the resuscitation device 102. As noted above, the gas-bag 110 is being pressed by the head 108 of the shaft 204 in this drawing, and thus is being compressed so as to cause the gas stored in the gas-bag 110 to be released via the valve 112.

Figure 3:
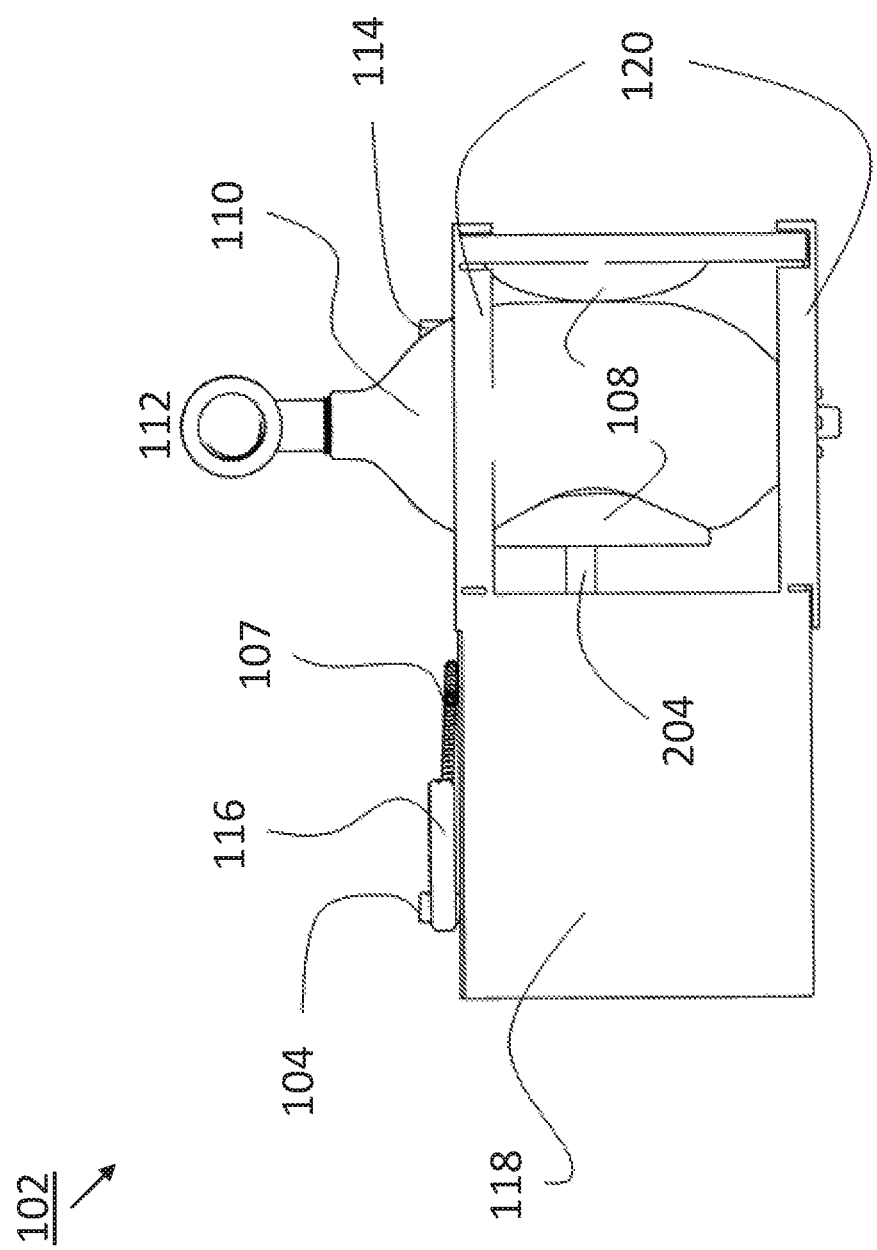
FIG. 3 illustrates another view of the resuscitation device, in accordance with some implementations of the current subject matter.

FIG. 3 illustrates another view of the resuscitation device 102. As noted above, the gas-bag 110 is being pressed by the head 108 of the shaft 204 in this drawing, and thus is being compressed so as to cause the gas stored in the gas-bag 110 to be released via the valve 112.

Figure 4:
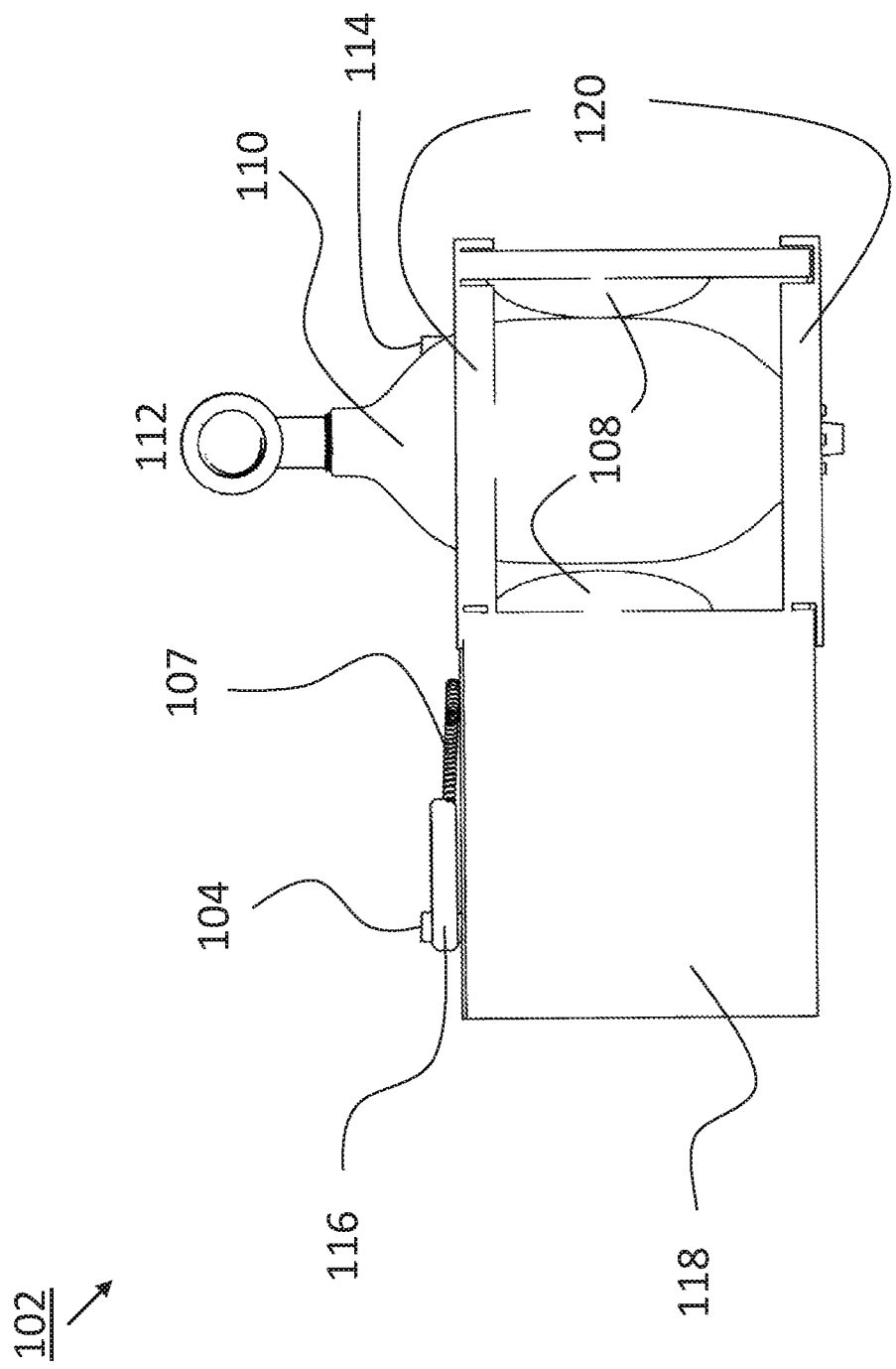
FIG. 4 illustrates another view of the resuscitation device, in accordance with some implementations of the current subject matter.

FIG. 4 illustrates another view of the resuscitation device 102, where the gas-bag 110 is not being pressed by the head 108 of the shaft 204.

Figure 5:
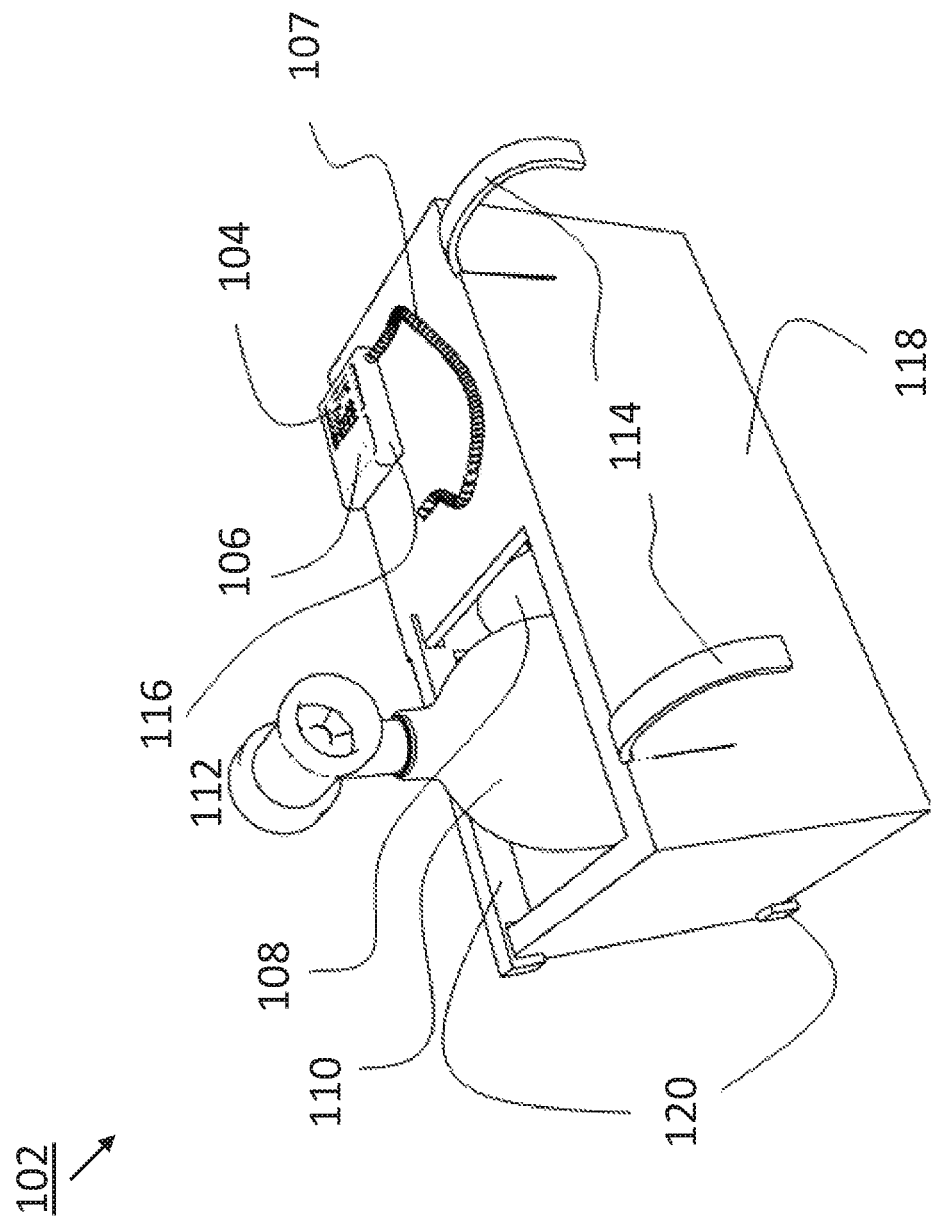
FIG. 5 illustrates another view of the resuscitation device, in accordance with some implementations of the current subject matter.

FIG. 5 illustrates another view of the resuscitation device 102.

Figure 6:
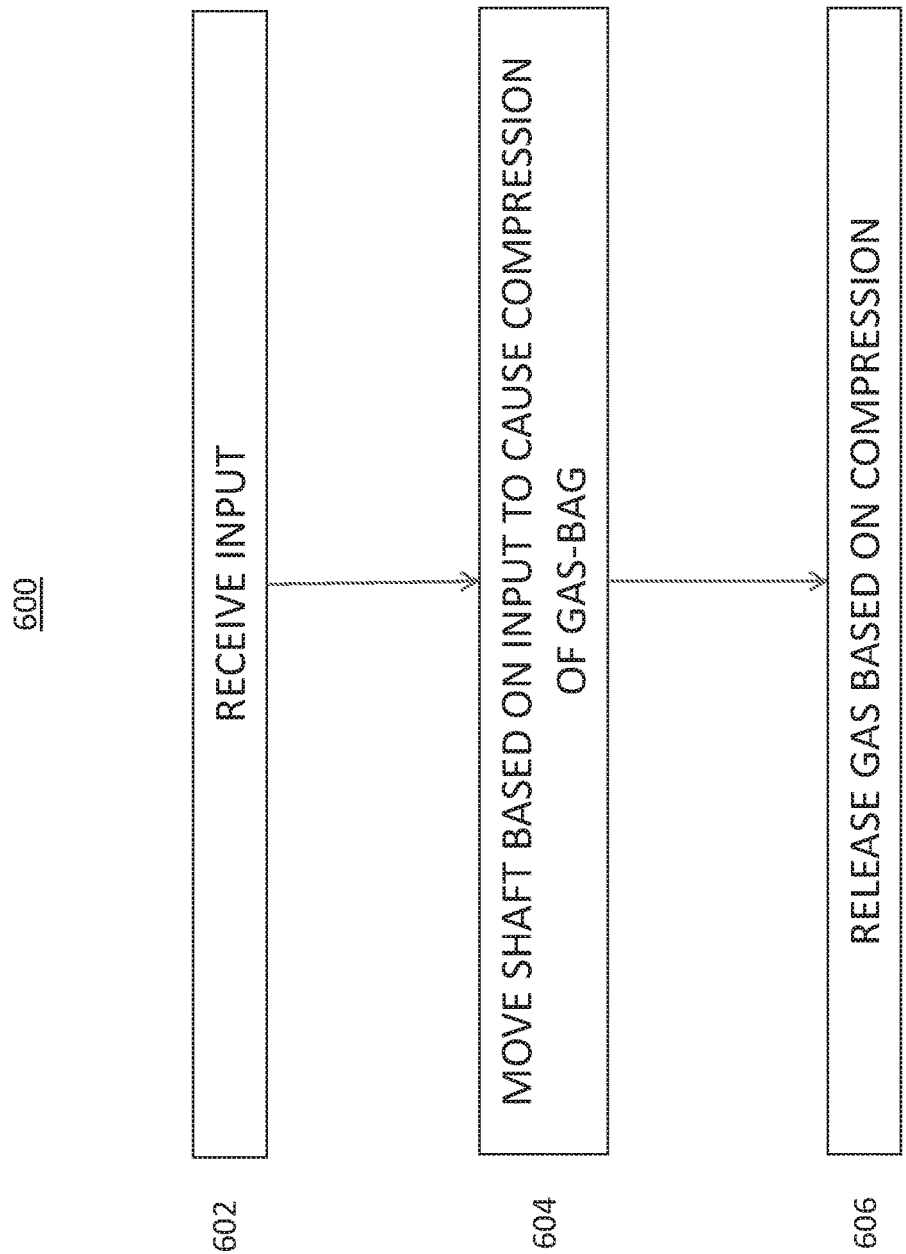
FIG. 6 is a flow-diagram illustrating operations of the resuscitation device, in accordance with some implementations of the current subject matter.

FIG. 6 is a flow-diagram illustrating operations of the resuscitation device 102. The programmable computer 104 can receive, at 602, an input to control a movement of the shaft 204. Based on the input, a controller on an electronic circuit board 202 can linearly move, at 604, the electromechanical structure 205, which in turn can linearly move the shaft 204, which has the head 108. The movement of the head 108 can cause the head 108 to press against the gas-bag 110 to compress the gas-bag 110. The gas-bag 110, upon being compressed, can release, at 606, gas via the valve 112. The valve 112 can include a filter configured to purify the released gas. The gas-bag 110 can be attached to a gas cylinder, which can fill the gas-bag with additional gas after the release of gas.

The programmable computer 104 can display, on a display screen 106, a pressure of the released gas and a frequency at which the gas is released. The input received at 602 to control the movement of the shaft 204 can include specifications of a desired pressure at which the gas is to be released and a desired frequency at which the gas is to be released.

Figure 7:
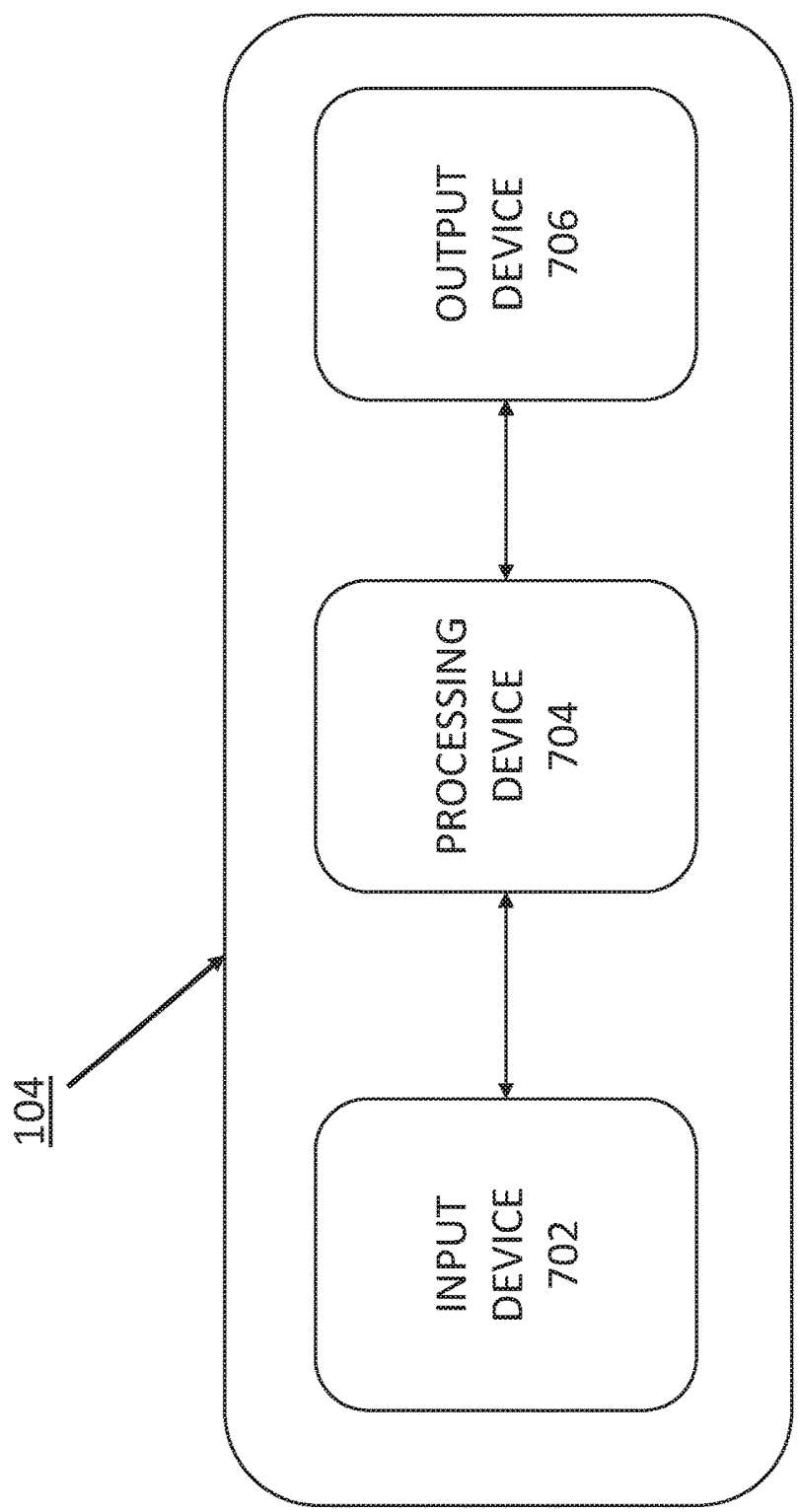
FIG. 7 illustrates one example of the components within the programmable computer, in accordance with some implementations of the current subject matter.

FIG. 7 illustrates one example of the components within the programmable computer 104. The programmable computer 104 can include: an input device 702, a processing device 704, and an output device 706. The programmable computer 104 can be enclosed in the first housing, as noted above. The first housing 116 can: be easy to open and close; be large enough to fit within it the input device 702, the processing device 704, and the output device 706; and have exhaust fans to protect the programmable computer from overheating.

The input device 702 can be a keyboard. Although a keyboard is described, in alternate implementations the input device 702 can be a mouse, a trackball, a joystick, a microphone, a tactile input device, a camera, or any other input device.

The processing device 704 can include some or all of a power supply, a motherboard, at least one expansion slot, a central processing unit (CPU), a memory, a video card, and a storage disk. The power supply can provide power to the motherboard and the expansion slots. The motherboard can electronically connect all of the components of the processing device 704 with the input device 702 and the output device 706. The expansion slot can be a socket on the motherboard that is used to insert an expansion card (i.e., circuit board), which provides additional features to the programmable computer, such as video, sound, advanced graphics, Ethernet, or additional memory. The CPU can include one or more processors. In alternate implementations where multi-core processors are used, there can be two or more CPUs on a single chip. The memory can be random access memory, which can work when the programmable computer 104 is on, and may be flushed out when the programmable computer 104 is turned off. The video card can be separate from the video card on the motherboard. The storage disk can be a hard disk drive or a solid state drive/disk.

The output device 706 can be the display screen 106. The display screen 106 can be a cathode ray tube (CRT) screen, a liquid crystal display (LCD) screen, a light emitting diode (LED) screen, or a screen with any other technology. While the output device 706 is described as the display screen 106, in alternate implementations the output device 706 can be a printer, an auditory output device, a tactile output device, or any other output device.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. These computer programs can be executable and/or interpreted on a programmable system. The programmable system can include at least one programmable processor, which can have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language. As can be used herein, the term "machine-readable medium" can refer to any computer program product, apparatus and/or device (for example, magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

To provide for interaction with a user, the subject matter described herein can be implemented on a computer that can display data to one or more users on a display device, such as a cathode ray tube (CRT) device, a liquid crystal display (LCD) monitor, a light emitting diode (LED) monitor, or any other display device. The computer can receive data from the one or more users via a keyboard, a mouse, a trackball, a joystick, or any other input device. To provide for interaction with the user, other devices can also be provided, such as devices operating based on user feedback, which can include sensory feedback, such as visual feedback, auditory feedback, tactile feedback, and any other feedback. The input from the user can be received in any form, such as acoustic input, speech input, tactile input, or any other input.

The subject matter described herein can be implemented in a computing system that can include at least one of a back-end component, a middleware component, a front-end component, and one or more combinations thereof. The back-end component can be a data server. The middleware component can be an application server. The front-end component can be a client computer having a graphical user interface or a web browser, through which a user can interact with an implementation of the subject matter described herein. The components of the system can be interconnected by any form or medium of digital data communication, such as a communication network. Examples of communication networks can include a local area network, a wide area network, internet, intranet, BLUETOOTH network, infrared network, or other networks.

Although a few variations have been described in detail above, other modifications can be possible. For example, the logic flows depicted in the accompanying figures and described herein do not require the particular order shown, or sequential order, to achieve desirable results. Additionally, dimensions of various components have been provided. These dimensions are examples, and alternates for each dimension may be possible. For example, in other implementations, each dimension may have an alternative value that can range from minus ten percent (i.e., −10%) of that dimension to plus ten percent (i.e., +10%) of that dimension. Additionally, dimensions of each component can be scaled up or down to ensure a proper fit of that component with any other element/component.

Other embodiments may be within the scope of the following claims.

What is claimed is:

1. A resuscitation device comprising:
    a housing;
    an electronic circuit board;
    a shaft that is operably coupled with the electronic circuit board and has a head, the electronic circuit board configured to actuate the shaft to move, the shaft being configured to move in a direction in which the head moves;
    a gas-bag adjacent to the head and configured to store gas, the moving of the shaft causing the head to move in a single dimension along a surface of the housing to compress the gas-bag, the single dimension being in a direction of an axis of the shaft, wherein the gas-bag is configured to extend outside the housing through at least one opening that is perpendicular to the axis of the shaft;
    another head that is immovable relative to the housing, wherein the moving of the head causes the gas-bag to be pressed against the other head; and
    a valve operably coupled to the gas-bag, the compression of the gas-bag causing the gas-bag to release gas.

2. The resuscitation device of claim 1, further comprising a programmable computer configured to receive an input, the programmable computer operably coupled to the electronic circuit board, the electronic circuit board actuating the shaft to move upon the receipt of the input.

3. The resuscitation device of claim 2, wherein the programmable computer receives the input from a user.

4. The resuscitation device of claim 2, wherein the programmable computer receives the input from a computer of a clinician via a communication network.

5. The resuscitation device of claim 2, wherein at least one of the programmable computer and the electronic circuit board is configured to control a pressure of the released gas and a frequency at which the gas is released.

6. The resuscitation device of claim 2, wherein the programmable computer and the electronic circuit board are operably coupled via a wired connection.

7. The resuscitation device of claim 2, wherein the programmable computer is configured to display, on a graphical user interface, a pressure of the released gas and a frequency at which the gas is released.

8. The resuscitation device of claim 2, wherein the programmable computer is configured to receive another input that controls the movement of the shaft, the movement of the shaft controlling a pressure of the released gas and a frequency at which the gas is released.

9. The resuscitation device of claim 1, further comprising a mask operably coupled to a gas cylinder attached to the gas-bag, the mask configured to interface with at least one of a mouth and a nose of a patient.

10. The resuscitation device of claim 1, further comprising an endotracheal tube operably coupled to a gas cylinder attached to the gas-bag, the endotracheal tube configured to be intubated into a patient.

11. The resuscitation device of claim 1, further comprising a gas cylinder attached to the gas-bag, the gas cylinder configured to fill the gas-bag with gas at predetermined intervals of time after the gas-bag has released gas.

12. The resuscitation device of claim 1, further comprising one or more clips configured to attach with a railing of at least one of a bed and a stretcher.

13. The resuscitation device of claim 1, wherein the valve includes a filter configured to purify the gas being released by the gas-bag, wherein the filter is located within two inches from a point-of-use of the resuscitation device that is configured to be used by a user.

14. A method comprising:
    receiving, at a programmable computer of a device, an input to control movement of a shaft within the device, the shaft having a head configured to move in a straight path in a first direction along a surface of a housing of the device, the device comprising another head that is immovable relative to the housing of the device;
    moving, based on the input and by a controller on an electronic circuit board wired to the programmable computer, the shaft with the head, the movement of the shaft causing the head to press against a gas-bag within the device to compress the gas-bag, the movement of the head further causing the gas-bag to be pressed against the other head, wherein the gas-bag extends outside the housing through at least one opening in a second direction that is different from the first direction; and
    releasing, by the gas-bag, gas when the gas-bag has been compressed.

15. The method of claim 14, wherein the gas is released by the gas-bag via a valve operably coupled to the gas-bag.

16. The method of claim 14, further comprising filling, by a gas cylinder attached to the gas-bag, the gas-bag with additional gas after the release of gas.

17. The method of claim 14, wherein:
    the input includes a height of a patient, a weight of the patient, and a type of the patient, the type of the patient being one of neonatal, pediatric, and adult; and
    at least one of the programmable computer or the electronic circuit board is configured to control, based on the input, a pressure of the released gas and a frequency at which the gas is released.

18. The method of claim 14, further comprising displaying, by a graphical user interface of the programmable computer, a pressure of the released gas and a frequency at which the gas is released.

19. The method of claim 14, wherein the gas-bag is locked in place using one or more detachable rods of the device.

20. The method of claim 14, wherein each of the head and the other head have a D-shape, wherein the other head is fixed to the housing of the device, wherein the shaft is configured to move in a direction in which the head moves.

* * * * *